(12) United States Patent
Coppes et al.

(10) Patent No.: US 7,563,284 B2
(45) Date of Patent: Jul. 21, 2009

(54) INTERVERTEBRAL DISC IMPLANT

(75) Inventors: Justin K. Coppes, West Chester, PA (US); David Gerber, West Chester, PA (US); David C. Paul, Phoenixville, PA (US); Andrew Lee, Orland, PA (US)

(73) Assignee: Synthes USA, LLC, West Chester, PA (US)

( * ) Notice: Subject to any disclaimer, the term of this patent is extended or adjusted under 35 U.S.C. 154(b) by 869 days.

(21) Appl. No.: 11/056,034

(22) Filed: Feb. 11, 2005
(Under 37 CFR 1.47)

(65) Prior Publication Data

US 2005/0197702 A1    Sep. 8, 2005

Related U.S. Application Data

(63) Continuation of application No. PCT/US03/25535, filed on Aug. 15, 2003.

(60) Provisional application No. 60/403,356, filed on Aug. 15, 2002, provisional application No. 60/403,402, filed on Aug. 15, 2002.

(51) Int. Cl.
*A61F 2/44* (2006.01)
(52) U.S. Cl. .................................. 623/17.12
(58) Field of Classification Search .... 623/17.11–17.16
See application file for complete search history.

(56) References Cited

U.S. PATENT DOCUMENTS

| 3,486,505 A | 12/1969 | Morrison |
| 3,867,728 A | 2/1975 | Stubstad et al. |
| 3,875,595 A | 4/1975 | Froning |
| 4,309,777 A | 1/1982 | Patil |
| 4,349,921 A | 9/1982 | Kuntz |
| 4,545,374 A | 10/1985 | Jacobson |
| 4,759,766 A | 7/1988 | Buettner-Janz et al. |
| 4,759,769 A | 7/1988 | Hedman et al. |

(Continued)

FOREIGN PATENT DOCUMENTS

DE    30 23 353    4/1981

(Continued)

OTHER PUBLICATIONS

International Search Report for PCT/US2003/025535 dated Dec. 8, 2003.

*Primary Examiner*—Bruce E Snow
(74) *Attorney, Agent, or Firm*—Stroock & Stroock & Lavan LLP

(57) ABSTRACT

The invention relates to an artificial intervertebral disc for placement between adjacent vertebrae. The artificial intervertebral disc is preferably designed to restore disc height and lordosis, allow for a natural range of motion, absorb shock and provide resistance to motion and axial compression. Furthermore, the intervertebral disc may be used in the cervical, the thoracic, or the lumber regions of the spine. The artificial intervertebral disc may include either singularly or in combination: an interior at least partially filled with a fluid; a valve for injecting fluid into the interior of the disk; a central region having a stiffness that is preferably greater than the stiffness of the outer regions thus enabling the disc to pivot about the central region. The central pivot may be formed by a center opening, a central chamber, an inner core or a central cable.

16 Claims, 8 Drawing Sheets

U.S. PATENT DOCUMENTS

| | | | |
|---|---|---|---|
| 4,772,287 A | 9/1988 | Ray et al. .................... 623/17 | |
| 4,834,757 A | 5/1989 | Brantigan | |
| 4,863,477 A | 9/1989 | Monson | |
| 4,878,915 A | 11/1989 | Brantigan | |
| 4,898,161 A | 2/1990 | Grundei | |
| 4,904,260 A | 2/1990 | Ray et al. .................... 623/17 | |
| 4,911,718 A | 3/1990 | Lee et al. | |
| 4,932,969 A | 6/1990 | Frey et al. | |
| 4,932,975 A | 6/1990 | Main et al. | |
| 4,946,378 A | 8/1990 | Hirayama et al. | |
| 4,997,432 A | 3/1991 | Keller | |
| 5,002,576 A | 3/1991 | Fuhrmann et al. | |
| 5,020,519 A | 6/1991 | Hayes et al. | |
| 5,041,139 A | 8/1991 | Branemark | |
| 5,071,437 A | 12/1991 | Steffee | |
| 5,122,130 A | 6/1992 | Keller | |
| 5,123,926 A | 6/1992 | Pisharodi | |
| 5,171,280 A | 12/1992 | Baumgartner | |
| 5,171,281 A | 12/1992 | Parsons et al. | |
| 5,192,327 A | 3/1993 | Brantigan | |
| 5,236,460 A | 8/1993 | Barber .................... 623/17 | |
| 5,246,458 A | 9/1993 | Graham | |
| 5,258,031 A | 11/1993 | Salib et al. | |
| 5,314,477 A | 5/1994 | Marnay | |
| 5,320,644 A | 6/1994 | Baumgartner | |
| 5,330,472 A | 7/1994 | Metz-Stavenhagen | |
| 5,360,430 A | 11/1994 | Lin | |
| 5,370,697 A | 12/1994 | Baumgartner | |
| 5,401,269 A | 3/1995 | Buttner-Janz et al. | |
| 5,409,492 A | 4/1995 | Jones et al. | |
| 5,423,816 A | 6/1995 | Lin | |
| 5,425,772 A | 6/1995 | Brantigan | |
| 5,425,773 A | 6/1995 | Boyd et al. | |
| 5,431,658 A | 7/1995 | Moskovich | |
| 5,458,638 A | 10/1995 | Kuslich et al. | |
| 5,458,642 A | 10/1995 | Beer et al. | |
| 5,458,643 A | 10/1995 | Oka et al. | |
| 5,505,732 A | 4/1996 | Michelson | |
| 5,507,816 A | 4/1996 | Bullivant | |
| 5,514,180 A | 5/1996 | Heggeness et al. | |
| 5,522,899 A | 6/1996 | Michelson | |
| 5,534,029 A | 7/1996 | Shima | |
| 5,534,030 A | 7/1996 | Navarro et al. | |
| 5,554,191 A | 9/1996 | Lahille et al. | |
| 5,556,431 A | 9/1996 | Buttner-Janz | |
| 5,562,736 A | 10/1996 | Ray et al. | |
| 5,562,738 A | 10/1996 | Boyd et al. | |
| 5,571,109 A | 11/1996 | Bertagnoli | |
| 5,591,235 A | 1/1997 | Kuslich | |
| 5,593,445 A | 1/1997 | Waits | |
| 5,609,636 A | 3/1997 | Kohrs et al. | |
| 5,609,637 A | 3/1997 | Biedermann et al. | |
| 5,658,337 A | 8/1997 | Kohrs et al. | |
| 5,669,909 A | 9/1997 | Zdeblick et al. | |
| 5,674,294 A | 10/1997 | Bainville et al. | |
| 5,674,296 A | 10/1997 | Bryan et al. | |
| 5,676,701 A | 10/1997 | Yuan et al. | |
| 5,676,702 A | 10/1997 | Ratron | |
| 5,683,465 A | 11/1997 | Shinn et al. | |
| 5,702,449 A | 12/1997 | McKay | |
| 5,702,450 A | 12/1997 | Bisserie | |
| 5,716,415 A | 2/1998 | Steffee | |
| 5,722,977 A | 3/1998 | Wilhelmy | |
| 5,755,796 A | 5/1998 | Ibo et al. | |
| 5,776,202 A | 7/1998 | Copf et al. | |
| 5,782,830 A | 7/1998 | Farris | |
| 5,782,832 A | 7/1998 | Larsen et al. | |
| 5,800,438 A | 9/1998 | Tuke et al. | |
| 5,824,094 A | 10/1998 | Serhan et al. | |
| 5,827,328 A | 10/1998 | Buttermann | |
| 5,865,846 A | 2/1999 | Bryan et al. | |
| 5,885,300 A | 3/1999 | Tokuhashi et al. | |
| 5,888,223 A | 3/1999 | Bray, Jr. | |
| 5,888,226 A | 3/1999 | Rogozinski | |
| 5,893,889 A | 4/1999 | Harrington | |
| 5,895,428 A | 4/1999 | Berry | |
| 5,899,941 A | 5/1999 | Nishijima et al. | |
| 5,928,284 A | 7/1999 | Mehdizadeh | |
| 5,935,151 A | 8/1999 | Broughton et al. | |
| 5,951,564 A | 9/1999 | Schroder et al. | |
| 5,989,291 A | 11/1999 | Ralph et al. | |
| 6,001,130 A | 12/1999 | Bryan et al. | |
| 6,017,342 A | 1/2000 | Rinner | |
| 6,019,792 A | 2/2000 | Cauthen | |
| 6,039,763 A | 3/2000 | Shelokov | |
| 6,042,582 A | 3/2000 | Ray | |
| 6,045,579 A | 4/2000 | Hochshuler et al. | |
| 6,063,088 A | 5/2000 | Winslow | |
| 6,063,121 A | 5/2000 | Xavier et al. | |
| 6,080,155 A | 6/2000 | Michelson | |
| 6,080,193 A | 6/2000 | Hochshuler et al. | |
| 6,083,225 A | 7/2000 | Winslow et al. | |
| 6,093,205 A | 7/2000 | McLeod et al. | |
| 6,113,602 A | 9/2000 | Sand | |
| 6,113,637 A | 9/2000 | Gill et al. | |
| 6,113,639 A | 9/2000 | Ray et al. | |
| 6,126,674 A | 10/2000 | Janzen | |
| 6,136,031 A | 10/2000 | Middleton | |
| 6,139,579 A | 10/2000 | Steffee et al. | |
| 6,143,031 A | 11/2000 | Knothe et al. | |
| 6,146,421 A | 11/2000 | Gordon et al. | |
| 6,146,422 A | 11/2000 | Lawson | |
| 6,156,067 A | 12/2000 | Bryan et al. | |
| 6,159,215 A | 12/2000 | Urbahns et al. | |
| 6,162,252 A | 12/2000 | Kuras et al. | |
| 6,168,601 B1 | 1/2001 | Martini | |
| 6,171,339 B1 | 1/2001 | Houfburg et al. | |
| 6,174,311 B1 | 1/2001 | Branch et al. | |
| 6,179,874 B1 | 1/2001 | Cauthen | |
| 6,187,043 B1 | 2/2001 | Ledergerber .................... 623/8 | |
| 6,193,757 B1 | 2/2001 | Foley et al. | |
| 6,224,607 B1 | 5/2001 | Michelson | |
| 6,228,118 B1 | 5/2001 | Gordon | |
| 6,231,609 B1 | 5/2001 | Mehdizadeh | |
| 6,238,414 B1 | 5/2001 | Griffiths | |
| 6,283,998 B1 | 9/2001 | Eaton .................... 623/17 | |
| 6,296,664 B1 | 10/2001 | Middleton | |
| 6,296,665 B1 | 10/2001 | Strnad et al. | |
| 6,315,797 B1 | 11/2001 | Middleton | |
| 6,319,257 B1 | 11/2001 | Carignan et al. | |
| 6,332,882 B1 | 12/2001 | Zucherman et al. | |
| 6,332,894 B1 | 12/2001 | Stalcup et al. ............ 623/17.11 | |
| 6,348,071 B1 | 2/2002 | Steffee et al. | |
| 6,368,350 B1 | 4/2002 | Erickson et al. | |
| 6,375,681 B1 | 4/2002 | Truscott | |
| 6,375,682 B1 | 4/2002 | Fleischmann et al. | |
| 6,375,683 B1 | 4/2002 | Crozet et al. | |
| 6,379,355 B1 | 4/2002 | Zucherman et al. | |
| 6,379,690 B2 | 4/2002 | Blanchard et al. | |
| 6,383,221 B1 | 5/2002 | Scarborough et al. | |
| 6,395,031 B1 | 5/2002 | Foley et al. | |
| 6,395,032 B1 | 5/2002 | Gauchet | |
| 6,402,784 B1 | 6/2002 | Wardlaw ................. 623/17.11 | |
| 6,402,785 B1 | 6/2002 | Zdeblick et al. | |
| 6,413,278 B1 | 7/2002 | Marchosky | |
| 6,416,551 B1 | 7/2002 | Keller | |
| 6,419,676 B1 | 7/2002 | Zucherman et al. | |
| 6,419,677 B2 | 7/2002 | Zucherman et al. | |
| 6,419,704 B1 | 7/2002 | Ferree | |
| 6,419,705 B1 | 7/2002 | Erickson ................. 623/17.16 | |
| 6,419,706 B1 | 7/2002 | Graf | |
| 6,425,920 B1 | 7/2002 | Hamada | |
| 6,436,119 B1 | 8/2002 | Erb et al. | |
| 6,440,142 B1 | 8/2002 | Ralph et al. | |

| | | |
|---|---|---|
| 6,440,168 B1 | 8/2002 | Cauthen |
| 6,440,169 B1 | 8/2002 | Elberg et al. |
| 6,454,806 B1 | 9/2002 | Cohen et al. |
| 6,468,310 B1 | 10/2002 | Ralph et al. |
| 6,478,796 B2 | 11/2002 | Zucherman et al. |
| 6,478,800 B1 | 11/2002 | Fraser et al. |
| 6,478,801 B1 | 11/2002 | Ralph et al. |
| 6,482,234 B1 | 11/2002 | Weber et al. ............. 623/17.12 |
| 6,506,151 B2 | 1/2003 | Estes et al. |
| 6,626,943 B2 | 9/2003 | Eberlein et al. .......... 623/17.15 |
| 6,645,248 B2 | 11/2003 | Casutt ..................... 623/17.12 |
| 6,712,853 B2 | 3/2004 | Kuslich ................... 623/17.16 |
| 6,733,533 B1 | 5/2004 | Lozier ..................... 623/17.12 |
| 6,893,465 B2 | 5/2005 | Huang ..................... 623/17.12 |
| 6,958,077 B2 | 10/2005 | Suddaby .................. 623/17.11 |
| 6,966,931 B2 | 11/2005 | Huang ..................... 623/17.16 |
| 6,969,405 B2 | 11/2005 | Suddaby .................. 623/17.12 |
| 6,984,246 B2 | 1/2006 | Huang ..................... 623/17.13 |
| 7,001,431 B2 | 2/2006 | Bao et al. ................. 623/17.12 |
| 7,056,345 B2 | 6/2006 | Kuslich ................... 623/17.16 |
| 7,066,958 B2 * | 6/2006 | Ferree ..................... 623/17.12 |
| 7,077,865 B2 | 7/2006 | Bao et al. ................. 623/17.12 |
| 7,156,877 B2 | 1/2007 | Lotz et al. ................ 623/17.16 |
| 7,166,130 B2 | 1/2007 | Ferree ..................... 623/17.15 |
| 2001/0010001 A1 | 7/2001 | Michelson |
| 2001/0012942 A1 | 8/2001 | Estes et al. |
| 2001/0016773 A1 | 8/2001 | Serhan et al. |
| 2001/0016775 A1 | 8/2001 | Scarborough et al. |
| 2001/0017343 A1 | 8/2001 | Ang et al. |
| 2001/0020170 A1 | 9/2001 | Zucherman et al. |
| 2001/0020186 A1 | 9/2001 | Boyce et al. |
| 2001/0032017 A1 | 10/2001 | Alfaro et al. |
| 2001/0051829 A1 | 12/2001 | Middleton et al. |
| 2002/0022888 A1 | 2/2002 | Serhan et al. |
| 2002/0029082 A1 | 3/2002 | Muhanna et al. |
| 2002/0035400 A1 | 3/2002 | Bryan et al. |
| 2002/0045904 A1 | 4/2002 | Fuss et al. |
| 2002/0045944 A1 | 4/2002 | Muhanna et al. ......... 623/17.16 |
| 2002/0058950 A1 | 5/2002 | Winterbottom et al. |
| 2002/0072752 A1 | 6/2002 | Zucherman et al. |
| 2002/0077702 A1 | 6/2002 | Castro |
| 2002/0082701 A1 | 6/2002 | Zdeblick et al. |
| 2002/0099377 A1 | 7/2002 | Zucherman et al. |
| 2002/0107573 A1 | 8/2002 | Steinberg ................. 623/17.12 |
| 2002/0111681 A1 | 8/2002 | Ralph et al. |
| 2002/0111682 A1 | 8/2002 | Ralph et al. |
| 2002/0111683 A1 | 8/2002 | Ralph et al. |
| 2002/0111684 A1 | 8/2002 | Ralph et al. |
| 2002/0111685 A1 | 8/2002 | Ralph et al. |
| 2002/0111686 A1 | 8/2002 | Ralph et al. |
| 2002/0111687 A1 | 8/2002 | Ralph et al. |
| 2002/0116006 A1 | 8/2002 | Cohen et al. |
| 2002/0116009 A1 | 8/2002 | Fraser et al. |
| 2002/0128714 A1 | 9/2002 | Manasas et al. |
| 2002/0128715 A1 | 9/2002 | Bryan et al. |
| 2002/0128716 A1 | 9/2002 | Cohen et al. |
| 2002/0130112 A1 | 9/2002 | Manasas et al. |
| 2002/0138079 A1 | 9/2002 | Cohen et al. |
| 2002/0143399 A1 | 10/2002 | Sutcliffe et al. |
| 2002/0156528 A1 | 10/2002 | Gau et al. |
| 2002/0156529 A1 | 10/2002 | Li et al. |
| 2002/0161366 A1 | 10/2002 | Robie et al. |
| 2002/0161375 A1 | 10/2002 | Ralph et al. |
| 2002/0161446 A1 | 10/2002 | Bryan et al. |
| 2002/0188295 A1 | 12/2002 | Martz et al. |
| 2002/0198598 A1 | 12/2002 | Pepper et al. |
| 2003/0004572 A1 | 1/2003 | Goble et al. |
| 2003/0004576 A1 | 1/2003 | Thalgott et al. |
| 2003/0009223 A1 | 1/2003 | Fehling et al. |
| 2003/0009224 A1 | 1/2003 | Kuras |
| 2003/0009225 A1 | 1/2003 | Khandkar et al. |
| 2003/0018389 A1 | 1/2003 | Castro et al. |
| 2003/0028251 A1 | 2/2003 | Mathews .................. 623/17.16 |
| 2003/0055427 A1 | 3/2003 | Graf |
| 2003/0069639 A1 | 4/2003 | Sander et al. ............. 623/17.11 |
| 2004/0133280 A1 | 7/2004 | Trieu ........................ 623/17.16 |
| 2004/0230309 A1 | 11/2004 | DiMauro et al. .......... 623/17.12 |
| 2004/0267369 A1 | 12/2004 | Lyons et al. .............. 623/17.16 |
| 2005/0033437 A1 | 2/2005 | Bao et al. ................. 623/17.15 |
| 2005/0085916 A1 * | 4/2005 | Li et al. .................... 623/17.16 |
| 2005/0119752 A1 | 6/2005 | Williams et al. .......... 623/17.16 |
| 2005/0177239 A1 | 8/2005 | Steinberg ................. 623/17.12 |
| 2005/0192671 A1 | 9/2005 | Bao et al. ................. 623/17.14 |
| 2005/0197701 A1 | 9/2005 | Steinberg ................. 623/17.12 |
| 2007/0250169 A1 | 10/2007 | Lang ........................ 623/17.12 |

FOREIGN PATENT DOCUMENTS

| | | |
|---|---|---|
| DE | 268 156 | 5/1989 |
| DE | 37 41 493 | 6/1989 |
| DE | 41 09 941 | 10/1992 |
| DE | 42 13 771 | 9/1993 |
| DE | 195 42 116 | 5/1997 |
| DE | 200 12 549 | 10/2000 |
| DE | 101 30 825 | 3/2002 |
| EP | 0 077 159 | 4/1983 |
| EP | 0 392 076 | 10/1990 |
| EP | 0 610 837 | 8/1994 |
| EP | 0 699 426 | 3/1996 |
| EP | 0 820 731 | 1/1998 |
| EP | 0 955 021 | 11/1999 |
| EP | 1 045 669 | 10/2000 |
| EP | 1 103 237 | 11/2000 |
| EP | 1 157 675 | 5/2001 |
| EP | 1 222 903 | 10/2001 |
| EP | 1 212 992 | 11/2001 |
| FR | 2 681 525 | 3/1993 |
| FR | 2 718 635 | 10/1995 |
| FR | 2 723 841 | 3/1996 |
| FR | 2 728 158 | 6/1996 |
| FR | 2 775 587 | 9/1999 |
| FR | 2 784 291 | 4/2000 |
| FR | 2 801 782 | 6/2001 |
| JP | 04099570 | 3/1992 |
| WO | WO 90/11740 | 10/1990 |
| WO | WO 94/04100 | 3/1994 |
| WO | WO 94/26213 | 11/1994 |
| WO | WO 99/00074 | 1/1999 |
| WO | WO 99/11203 | 3/1999 |
| WO | WO 99/20209 | 4/1999 |
| WO | WO 99/42062 | 8/1999 |
| WO | WO 99/53871 | 10/1999 |
| WO | WO 99/62439 | 12/1999 |
| WO | WO 00/04851 | 2/2000 |
| WO | WO 00/13619 | 3/2000 |
| WO | WO 00/13620 | 3/2000 |
| WO | WO 00/35382 | 6/2000 |
| WO | WO 00/35383 | 6/2000 |
| WO | WO 00/35384 | 6/2000 |
| WO | WO 00/35385 | 6/2000 |
| WO | WO 00/35387 | 6/2000 |
| WO | WO 00/74606 | 12/2000 |
| WO | WO 01/01893 | 1/2001 |
| WO | WO 01/06962 | 2/2001 |
| WO | WO 01/19295 | 3/2001 |
| WO | WO 01/64140 | 9/2001 |
| WO | WO 01/68003 | 9/2001 |

* cited by examiner

INTERVERTEBRAL DISC IMPLANT

CROSS REFERENCE TO RELATED APPLICATION

The present application is a continuation of International Patent Application PCT/US03/25535 filed Aug. 15, 2003, which claims priority from U.S. application Ser. No. 60/403,356 filed on Aug. 15, 2002 and U.S. application Ser. No. 60/403,402 filed on Aug. 15, 2002, the entire contents of which are expressly incorporated herein by reference thereto.

FIELD OF THE INVENTION

The invention is related to devices and methods for the treatment of trauma and diseases of the spine. More particularly, the invention relates to intervertebral disc replacement.

BACKGROUND OF THE INVENTION

A variety of conditions such as spondylolysis, disc herniation, compression of spinal cord nerve roots, degenerative disc disease, and trauma are known to cause severe discomfort, requiring medical attention. Among the procedures currently used to alleviate such conditions are spinal fusion, such as intervertebral and posterolateral fusion or arthrodesis. In these procedures, two adjacent vertebral bodies are fused together. The affected intervertebral disc is first excised, and an implant is inserted which accommodates bone growth between the two vertebral bodies to effectively bridge the gap left by the disc removal. A number of different implant materials and implant designs have been used for fusion with varying success. Although intervertebral and posterolateral fusion are widely used, drawbacks to their use include a reduced physiologic range of motion and other fusion related complications such as degeneration of adjacent discs and destabilization of the functional spinal unit. As a result, alternative treatments with fewer complications, but similar efficacy to fusion, are desirable. One such alternative to spinal fusion is arthroplasty and the use of a prosthetic or artificial disc.

In general, arthroplasty is used in the replacement of diseased joints. Arthroplasty involves a set of procedures directed to maintaining motion of the joint, thereby preserving its integrity and keeping the adjacent motion segments from deteriorating, as they tend to do after fusion. Depending on the location and the condition of the affected joint, specific arthroplasty procedures may be used. For example, interpositional reconstruction surgery, which reshapes the joint and adds a prosthetic disk between the two bones forming the joint is commonly used on elbow, shoulder, ankle, and finger joints. Total joint replacement, or total joint arthroplasty, replaces the entire diseased joint with an artificial prosthesis and, in recent years, has become the operation of choice for most knee and hip problems.

Hip and knee replacements are particularly widespread with nearly 300,000 hip replacements and about as many knee replacements performed in the United States in 2001. With respect to the knee and hip joint replacement surgeries, there are several implants or prosthetics available. For the hip prosthetic, in an exemplary design, there are two components, one is a metal ball attached to a metal stem which is fitted into the femur, and the second is a matching plastic socket which is implanted into the pelvis. The metal pieces are generally formed from stainless steel, alloys of cobalt and chrome, titanium, and alloys of titanium; the plastic pieces are generally formed from high-density polyethylene. For the knee prosthetics, in an exemplary embodiment, metal and plastic components are again used to replace the damaged bone ends and cartilage. The metal pieces are generally formed from stainless steel, alloys of cobalt and chrome, titanium, and alloys of titanium; the plastic pieces are generally formed from high-density polyethylene.

Although the evolution of spinal arthroplasty and the use of prosthetics in the spine has been similar to that of other joints in the body, evolving from fusing the joint to replacement the functional joint, the advent of spinal arthroplasty, however, has been slower than arthroplasty in other major joints in the body. A few of the possible reasons why spinal arthroplasty has been delayed are that spinal problems related to disc degeneration are difficult to diagnose, spinal procedures are typically crisis-driven and thus conservative solutions such as fusion are acceptable, and spinal anatomy is complex.

Over the past 40 years spinal arthroplasty technologies have been under development and in the last 10 years spinal arthroplasty has won the attention of leading surgeons and implant manufacturers. The evolution of spinal arthroplasty essentially began in the 1950's and one of several emerging concepts was the spherical concept of the disc prostheses. The spherical concept is simply the placement of a ball, essentially circumferential, the cavity of the nucleus pulposus after a discectomy procedure has been performed. The annulus is kept in place and the ball serves as a nucleus replacement device. Various materials have been experimented with for the spherical concept. For example, in the early 1960's, implants using silicone ball bearings were implanted into the cervical regions of the patents, but the outcomes were uncertain. In the mid 1960's, stainless-steel (ball bearing) prostheses were implanted into patients. The results of the procedure were initially promising but over time the disc spaces lost height due to subsidence of the steel balls into the vertebral bodies. Presently, the concept of a spherical prosthesis continues to be examined using different materials, the latest of which is a modified carbon fiber.

Another emerging concept is the mechanical concept design. The mechanical concept design is essentially a total disc replacement product which is intended to restore the range of motion of the vertebral motion segment unit. These devices are often comprised of metallic endplates fixed to the adjacent vertebral bodies via a stabilization mechanism and a core formed from polyethylene or other polymeric materials. Alternatively, instead of a core, bearing surfaces can be used, the bearing surface materials being ceramic-on-ceramic, metal-on metal, or metal-on-polyethylene. The mechanical design concept is based on the same principles as joint reconstruction products, such as knee and hip replacements, and a variety of mechanical design prostheses concepts have been proposed and continue to be proposed.

Another concept is the physiological concept. The physiological concept uses a hydrogel, elastomer, or polyurethane-based core which is intended to restore the disc function by absorbing and emitting fluid between the patient's vertebral endplates, while also maintaining the natural shock absorbing or cushioning function of the disc. The physiological concept devices are generally considered only a partial solution as they are designed to replace only the nucleus or a portion of the disc.

All of the approaches to disc replacement are aimed at some or all of the following: alleviating discogenic pain, restoring range of motion, maintaining the natural shock absorbing function of the disc, restoring normal form or disc height, and storing physiological kinematics. Generally, four exemplary types of artificial intervertebral discs have been developed for replacing a portion or all of an excised disc:

elastomer/fluid filled discs, ball and socket type discs, mechanical spring discs and hybrid discs.

Elastomer/fluid filled discs typically include an elastomer cushion or a fluid filled chamber positioned between lower and upper rigid endplates. The cushions and chambers of these implants advantageously function, in mechanical behavior, similar to the removed intervertebral disc tissue.

Ball and socket type discs typically incorporate two plate members having cooperating inner ball and socket portions which permit articulating motion of the members during movement of the spine.

Mechanical spring discs typically incorporate one or more coiled springs disposed between metal endplates. The coiled springs define a cumulative spring constant that is designed to be sufficient to maintain the spaced arrangement of the adjacent vertebrae while allowing normal movement of the vertebrae during flexion and extension of the spine in any direction.

The fourth type of artificial intervertebral disc, the hybrid disc incorporates two or more of the aforementioned design principles. For example, one known hybrid disc arrangement includes a ball and socket joint surrounded by an elastomer ring.

While each of the foregoing prostheses addresses some of the problems relating to intervertebral disc replacement, each of the implants presents significant drawbacks. Thus, there is a need for an intervertebral implant that accommodates the anatomy and geometry of the intervertebral space sought to be filled as well as the anatomy and geometry of the ends of adjacent vertebral bodies, while providing reliability and simplicity in design. More particularly, there is a need for a spinal disc implant which provides stability for supporting the high loads applied to the vertebrae, permits sufficient mobility to allow the patient an approximate normal range of motion, provides for axial compression between adjacent vertebrae, and has shock absorption abilities.

SUMMARY OF THE INVENTION

The invention relates to an intervertebral disc that is preferably designed to restore disc height and lordosis, allow for a natural range of motion, absorb shock and provide resistance to motion and axial compression. Furthermore, the intervertebral disc may be used in the cervical, the thoracic, or the lumber regions of the spine.

The intervertebral disc includes a body having a footprint that is preferably conforming in size and shape with at least a portion of the ends of adjacent vertebrae. The shapes of the intervertebral disc include, but are not limited to, circular, oval, ellipsoid, kidney-bean, annular, C-shaped, D-shaped, etc.

In one embodiment, the body of the intervertebral disc includes an upper endplate, a lower endplate, and an elastic membrane disposed between the upper and lower endplates. Alternatively, the elastic membrane may surround and encapsulate the endplates. The elastic membrane defines an interior that is at least partially filled with a fluid. Preferably, the fluid is selected from the group consisting of a gas, a liquid, a gel or any combination thereof. In addition, the fluid may be compressible, and may be selected from the group consisting of, for example, gas, liquid, or hydrogel, or may be incompressible, and may be selected from the group consisting of, for example, saline.

The disc also preferably includes a valve for permitting insertion of fluid to the interior of the intervertebral disc. The valve may be disposed on the elastic membrane, alternatively, however the valve can be located in the upper and lower endplates of the disc.

The upper and lower endplates are preferably formed of metal, such as titanium, stainless steel, titanium alloys, cobalt-chromium alloys, or amorphous alloys. Alternatively, however, the upper and lower endplates may be formed of ceramics, composites, polymers, such as poly-ether-ether-ketone (i.e., PEEK) or an ultra high molecular weight polyethylene (i.e., UHMWPE), bone, including cortical, cancellous, allograft, autograft, xenograft, dimineralized or partially demineralized bone, or any other materials able to serve as load bearing supports. The materials chosen for the endplates, in combination with the desired fluid, are preferably selected to reduce the amount of wear, and thus increase the life of the joint.

The outer surface of the upper and lower endplates may be substantially flat, wedge-shaped, etc. The outer surfaces of the upper and lower endplates also may be dome shaped with their radii defined in the sagittal and coronal planes to generally match those of the ends of the adjacent vertebra. The dome shape allows the upper and lower endplates to better conform with the ends of the adjacent vertebrae for a better fit in situ.

The intervertebral disc also preferably includes migration-resistant structures provided on the outer surface of at least one or both of the endplates to impede movement, dislodging, or expulsion of the endplates within and from the ends of the adjacent vertebrae. The migration-resistant structures include, but are not limited to, flaps, spikes, teeth, fins, deployable spikes, deployable teeth, flexible spikes, flexible teeth, alternatively shaped teeth, insertable or expandable fins, screws, hooks, serrations, ribs, and textured surfaces.

Furthermore, the upper and lower endplates also preferably coated with a bone growth inducing or conducting substance to promote bony ingrowth to permanently secure the disc to the adjacent vertebrae. Alternatively, the upper and lower endplates may have a roughened surface; a porous surface; laser treated endplate layers; integrate an osteoconductive/osteoinductive scaffold; or may be provided with or made from an integral osteoconductive and/or osteoinductive material to promote bony ingrowth. The endplates may further include a membrane and/or a barrier to limit the amount and/or depth of bony ingrowth.

The upper and lower endplates may also have implant instrumentation attachment, guiding, and retainment structures. For example, the endplates may have holes, slots, threads, or a dovetail for implanting the implant and/or distracting the adjacent vertebrae. For example, the disc may include a slot formed in the upper and/or lower endplates, the slot being configured to receive an implant insertion instrument, a distractor or both.

The upper and lower endplates may also preferably include articulating surfaces, thus providing the intervertebral disc with greater mobility. The articulating surfaces preferably including a surface polish or similar wear reducing finish such as diamond finish, TiNi finish, etc. in order to minimize wear, decrease particle generation, and increase disc life.

In some embodiments, in addition to the fluid or in place of the fluid, additional structures may be included to provide additional stiffness. The structures include, but are not limited to, springs, elastomers, bellow, balloons, closed reservoirs, hollow bodies, biocompatible fibers, and cables.

In some embodiments, the intervertebral disc also preferably has an articulating mechanism to allow the endplates to pivot with respect to one another such that associated portions of the endplates may come closer together under compression while different associated portions of the endplates may separate under tension. The articulation mechanism may be in the form of a center pivot axis or fulcrum. Preferably, the intervertebral disc also allows and provides a mechanism, or is configured to allow the location of the pivot axis within the disc to change in response to the loading conditions, thus providing a moving instantaneous axis of rotation. The intervertebral disc also preferably comprises a mechanism, such as providing a fluid, an elastomer, a spring, a cable, etc. to absorb axial compression forces and to provide a shock absorbing effect.

In some embodiments the intervertebral disc includes an upper end, a lower end, and an outer sidewall disposed therebetween. The disc may have an interior volume defined between the upper and lower ends and the outer sidewall, with the interior volume preferably including a center pivot and at least one chamber, the chamber being peripheral to and surrounding the center pivot. Preferably, the center pivot includes a central wall defining a central chamber, and the at least one peripheral chamber is disposed between the outer sidewall and the central wall. A first fluid may be disposed in the at least one peripheral chamber. A second fluid may be disposed in the central chamber. The first and second fluids may or may not be the same. The intervertebral disc may include additional peripheral chambers which may or may not be in fluid communication with the central chamber and each other. Further, the sidewall may be formed of a first material while the central wall may be formed of a second material, with the first material having a different stiffness than the second material. Preferably, the center pivot and/or central chamber may permit the upper and lowers ends to pivot with respect to each other, and may include a resilient element such as a spring.

In another embodiment, the intervertebral disc includes a body having an upper surface spaced from and opposing a lower surface. The spacing between the upper surface and the lower surface may be selectable. The body further includes an outer sidewall forming an outer wall and a thru-hole forming an inner wall, with the inner wall defining an opening. Further, the body may be substantially C-shaped. A chamber may also be disposed within the body. In addition, there may be at least one portion extending from the body for contacting a vertebrae, with the portion defining a hole for receiving a fastener.

The intervertebral disc may be implanted in a modular fashion, if possible, or it may be implanted preassembled. An anterior, anteriolateral, or lateral surgical approach may be used to implant the intervertebral disc. Furthermore, depending on the intervertebral disc to be implanted, a minimally invasive surgical method or a simultaneous distraction and implantation surgical method may be used. Also depending on the intervertebral disc to be implanted, the Anterior Longitudinal Ligament may be attached directly to the disc or to the adjacent vertebral bodies. The Anterior Longitudinal Ligament may be formed from partially dimineralized or demineralized autograft, allograft, or xenograft. Alternatively, the Anterior Longitudinal Ligament may be formed from biocompatible materials such as elastomers, or braided polymers. To assist with the implantation of the intervertebral disc, the intervertebral disc may include alignment markers.

BRIEF DESCRIPTION OF THE DRAWINGS

To facilitate an understanding of and for the purpose of illustrating the present invention, exemplary and preferred features and embodiments are disclosed in the accompanying drawings, it being understood, however, that the invention is not limited to the precise arrangements and instrumentalities shown, and wherein similar reference characters denote similar elements throughout the several views, and wherein.

DETAILED DESCRIPTION OF THE PREFERRED EMBODIMENTS

Figure 1:
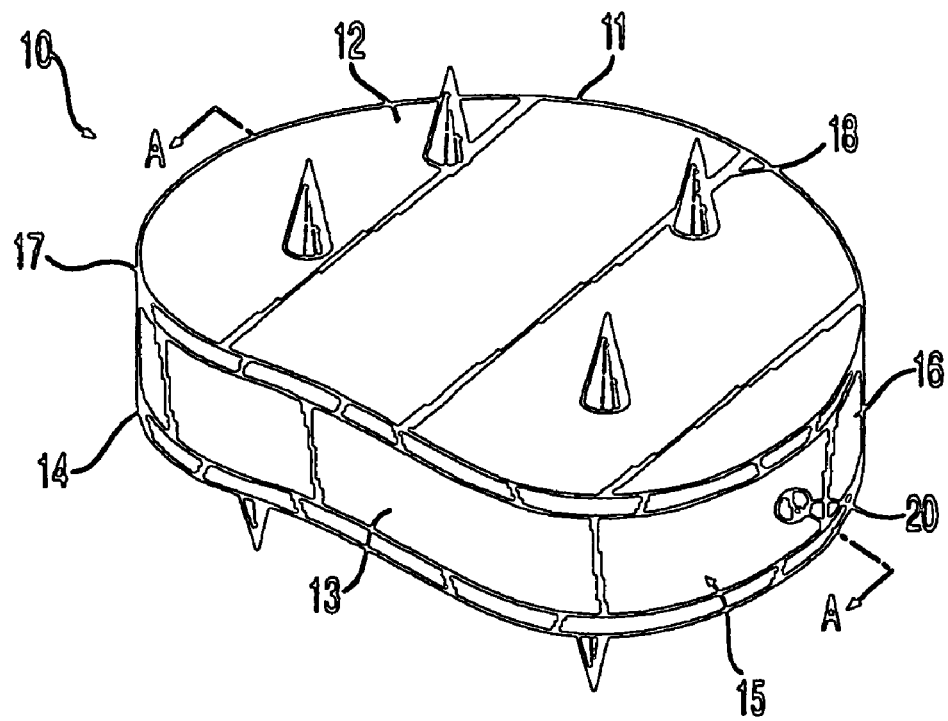
FIG. 1 is a perspective view of a first embodiment of an artificial intervertebral disc according to the present invention.

Any of a wide variety of different implant structures can be prepared according to the teachings shown by the illustrative examples of the intervertebral discs disclosed herein. The intervertebral discs of the present invention are preferably designed to store spinal lordosis, disc height, to allow for a natural range of motion, absorb shock and to provide resistance to motion and axial compression.

The intervertebral discs preferably are sized and adapted for use in the cervical, thoracic, and lumbar regions of the spine. Also, the intervertebral discs can be tailored for each individual patient allowing for disc characteristics appropriate for the individual patient. For example, the core of the disc can include different assemblies, different components, and/or various types of materials to create the desired characteristics for each individual patient.

Furthermore, the intervertebral discs may allow flexion, extension, lateral banding, rotation, and translation. Flexion is movement that brings two parts of a joint or body into a bent position; in the spine, this is a movement in which the spine starts straight and moves into forward bending. Extension is a movement that draws two parts away from each other, in the spine, this is a movement in which the spine starts straight and moves into backward bending. Lateral bending is a bending movement toward a lateral side; in the spine, this movement generally involves bending (lateral) and coupled rotation.

Rotation is a movement that results in a portion of the spine twisting, rotating or turning with respect to the axis of the spinal column. Translation is a limited movement that is generally transverse to the axis of the spinal column.

Additionally, similar to a natural intervertebral disc, the artificial intervertebral discs preferably allow for a moving instantaneous axis of rotation. At every instant for a body in plane motion there is a line in the body or a hypothetical extension of this line that does not move. The instantaneous side of rotation is this line. A moving instantaneous axis of rotation refers to the ability of the instantaneous axis of rotation to move (i.e., translate) as a result of different loading conditions; in other words, the location of the instantaneous axis of rotation moves with respect to the disc. The preferred mean location of the moving instantaneous axis of rotation for the lumber region of the spine is preferably in the posterior half of the disc space or proximal to an adjacent (superior or inferior) endplate, preferably proximal to the inferior/caudal endplate, the preferred mean location of the moving instantaneous axis of rotation for the thoracic region of the spine is preferably in the inferior portion of the disc space and proximal to the caudal vertebral body extending posteriorly into the spinal canal, and the preferred mean location of the moving instantaneous axis of rotation for the cervical region of the spine is preferably in the posterior half of the caudal vertebral body.

Also similar to a natural intervertebral disc, the response characteristics of the artificial intervertebral disc are preferably non-linear. For example, in response to continued axial compression, the artificial intervertebral disc preferably undergoes a large initial amount of compression followed by non-linearly decreasing amounts of compression.

Referring to the accompanying drawings, preferred embodiments and features of the artificial intervertebral disc will be described in detail. It is to be noted however that these descriptions of specific embodiments and features are merely illustrative. It is contemplated that one or more features or elements of the various embodiments may be combined or used singularly, and that modifications of the various embodiments, as well as other embodiments are contemplated and will be apparent to those persons skilled in the art.

Figure 2:
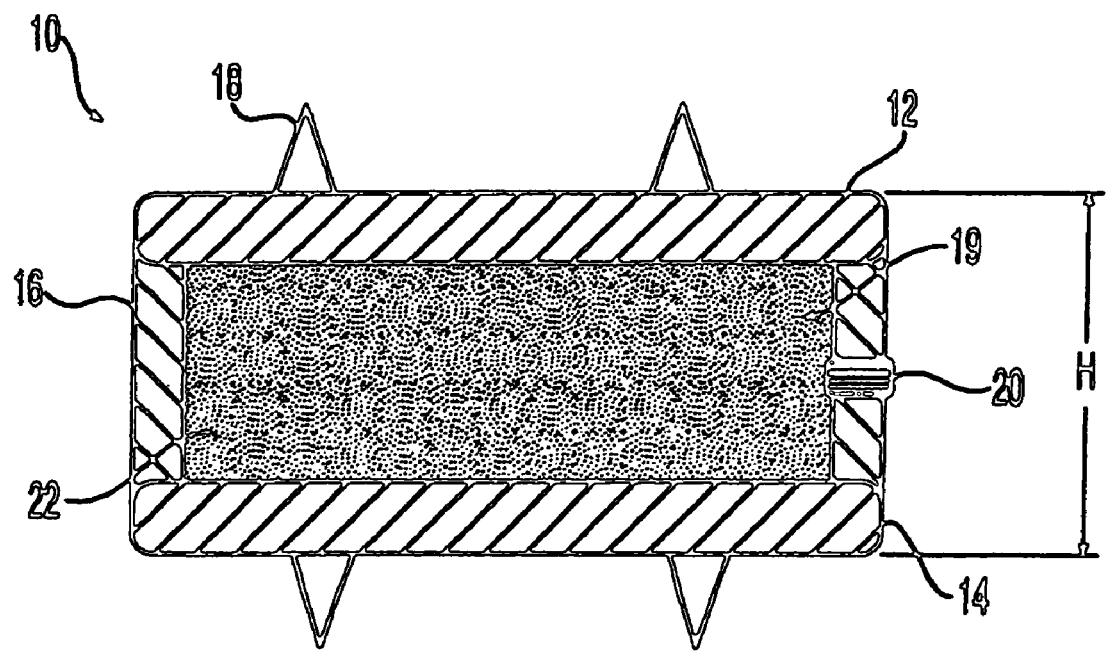
FIG. 2 is a cross-sectional view of the artificial intervertebral disc of FIG. 1 taken along line A-A.

Referring initially to FIGS. 1 and 2, a perspective view of an exemplary first embodiment of an artificial intervertebral disc 10 is shown. As shown, the disc 10 has a generally kidney-bean shaped footprint which includes an anterior side 11, a posterior side 13, and first and second lateral sides 15, 17, respectively. The anterior side 11 and lateral sides 15, 17 are all substantially convex in shape while the posterior side 13 is substantially concave in shape. However, the disc 10 may take on other shapes that preferably conform geometrically and anatomically with the adjacent vertebral bodies including, but not limited to circular, oval, ellipsoid, annular, D-shaped, C-shaped, etc.

As shown, the intervertebral disc 10 includes an upper endplate 12, a lower endplate 14 and an elastic membrane 16, the elastic membrane 16 generally extending from the upper endplate 12 to the lower endplate 14 and is located, preferably, proximate to the outer peripheray of the disc 10. Alternatively, the elastic membrane 16 may surround and/or encapsulate the upper and lower endplates 12, 14. The elastic membrane 16 in combination with the upper and lower endplates 12, 14 may define an interior volume that may be at least partially filled with a fluid 22. The elastic membrane 16 preferably is formed from an elastomer such as polyurethane, silicone, a braided polymer, or any other appropriate elastic material known in the art. The elastic membrane may be non-permeable. Alternatively the elastic membrane 16 may be permeable or semi-permeable to allow fluid to flow into and out of the interior of the disc (as described in more detail below). Preferably, the elastic membrane 16 may resist translational motion between the upper and lower endplates 12, 14, and may also prevent soft tissue ingrowth between the endplates 12, 14 as well as contain any wear particles generated within the interior volume. The elastic membrane 16 may be attached to the upper and lower endplates 12, 14 by an fixation method known in the art including, but not limited to, bonding agents, ultrasonic welding, screws, nails, mechanical wedging, and pins.

Alternatively, the elastic membrane 16 may be in the form of a bellow, the bellow assuming an "accordion" shape, enabling it to expand and contract under the various loading conditions. The bellow may be rigidly attached to the upper and lower endplates 12, 14 by an method known in the art including, but not limited to a circular groove formed in each endplate 12, 14, bonding agents, ultrasonic welding, screws, nails, mechanical wedging, and pins. Preferably, the bellow is made from a metal, although other material such as elastomers or polymers may be used.

Figure 2A:
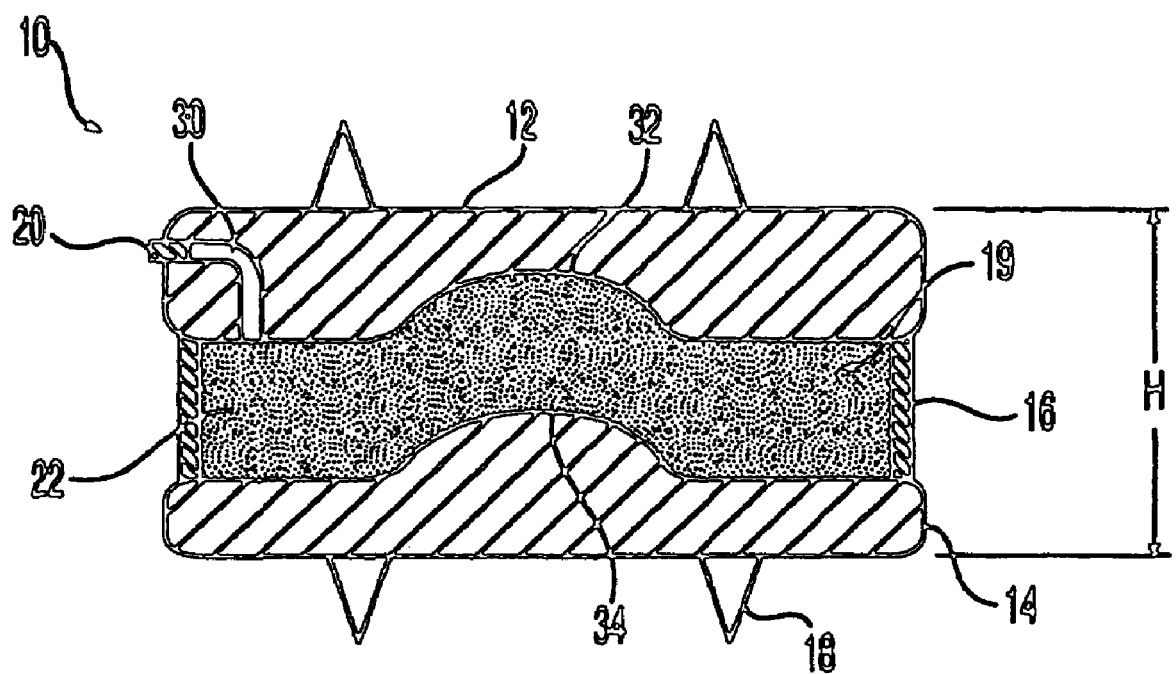
FIG. 2a is an alternate cross-sectional view of the artificial intervertebral disc of FIG. 1 taken along line A-A.

The disc 10 also may include a valve 20, the valve 20 providing access to the interior 19 of disc 10 so that fluid may be injected into, or removed from, the interior 19 of the disc 10. The valve 20 preferably is a one-way valve, as known to those skilled in the art, so that the fluid, once injected, can not escape from the interior 19 of the disc 10. As shown in FIGS. 1 and 2, the valve 20 preferably is disposed within the elastic membrane 16, alternatively however, the valve 20 may be disposed within the upper and/or lower endplates 12, 14, as shown in FIG. 2a. When the valve is disposed on the upper and/or lower endplates 12, 14, a passageway 30 preferably is included to interconnect the valve 20 with the interior 19 of the disc 10.

The fluid 22 provided in the interior volume may be a gas, a liquid, a gel, or any combination thereof. When a gas is provided as the fill media for the interior volume, or where a combination of gas and liquid or gel is provided, the ultimate gas pressure within the interior volume should be selected to provide adequate shock absorption during axial compression of the disc 10. The fluid may also permit limited articulation or movement of the upper endplate 12 and lower endplate 14 with respect to one another. Preferably, the fluid is an incompressible liquid, for example, a saline solution. In use, the fluid 22 may be injected into the interior 19 of the disc 10 before insertion of the disc 10 between adjacent vertebrae. Alternatively, the fluid 22 may be injected in situ to facilitate insertion of the disc 10 and subsequent distraction between adjacent vertebrae. The rigidity and distraction capabilities of the disc 10 may be a function of the amount of fluid 22 injected into the interior 19 of the disc 10 and/or the elastic nature of the membrane 16. Generally, the more fluid 22 provided in the interior 19 of the disc 10, the more rigid the disc 10, and the greater the distraction capability. Furthermore, pliability and increased articulation may be realized by filling only a portion of the interior volume 19 of the disc 10. Finally, variably filling the interior 19 of the disc 10 with fluid 22 permits the overall height H of the disc 10 to be varied as necessary depending on the needs of the individual patient.

As shown in FIG. 2a, the upper endplate 12 may have an inner surface provided with an arcuate socket 32, while the lower endplate 14 may have an inner surface provided with an arcuate protrusion 34, or vice versa. The socket 32 and protrusion 34 are configured and dimensioned to mate, or to correspond generally with each other. The type and amount of articulation desired may dictate the curvature of the socket 32 and protrusion 34 provided. For example, if the protrusion 34 has the same radius as the socket 32, then the disc 10 may provide greater support but more constrained movement. Alternatively, if the socket 32 has a larger radius than the protrusion 34, the disc will provide increased articulation. Furthermore, the protrusion 34 and/or socket 32 may also incorporate a flattened portion which may allow translational movement of the upper endplate 12 with respect to the lower endplate 14. By allowing translation, the disc 10 may provide a moving instantaneous axis of rotation as previously explained.

It is also possible for the socket 32 and protrusion 34 to take on contours other than those described above in order to achieve a desired articulation. Moreover, while the socket 32 and protrusion 34 are shown with contours that generally permit mating of their surfaces, it is possible to provide non-mating contours for the socket 32 and protrusion 34 to achieve a desired articulation.

The use of a fluid filled interior volume 19 in combination with an articulating surface may permit the socket 32 and protrusion 34 to translate more easily with respect to each other by reducing friction between the sliding surfaces.

Alternatively, where the fluid is a compressed gas, the articulation surfaces may not be constantly engaged, but may only become engaged when sufficient compressive force is placed in the disc by the adjacent vertebrae. Thus, the disc of this embodiment would have a dual performance aspect, under one loading scenario performing like a fluid-filled disc, and under a second scenario performing like a mechanical protrusion/socket articulating disc.

Depending on the location in the spine where the disc 10 is implanted, the disc 10 preferably may restore height in the range from about 4 millimeters (mm) to about 26 mm. In addition, the disc 10 preferably may restore lordosis in the range between about 0° to about 20°. The disc 10 preferably may also restore stiffness in the range from about 1 Newton-meter per degree (Nm/deg) to about 11 Nm/deg in axial rotation, about 0 Nm/deg to about 7 Nm/deg in flexion/extension, and about 0 Nm/deg to about 5 Nm/deg in lateral bending. In addition, the disc 10 preferably provides a compression stiffness from about 100 N/mm to about 5000 N/mm and tension stiffness from about 50 N/mm to about 1000 N/mm. Furthermore, depending on the location of the spine where the disc 10 is implanted, the intervertebral disc 10 preferably allows for a range of motion of from about 5° to about 45° in flexion/extension, from about 3° to about 33° in lateral bending, and from about 1° to about 60° in axial rotation. The intervertebral disc 10 preferably also allows for axial compression in the range from about 0.2 mm to about 2 mm.

Preferably, the upper and lower endplates 12, 14 are formed of metal, such as titanium, stainless steel, titanium alloys, cobalt-chromium alloys, or amorphous alloys. Alternatively, however, the upper and lower endplates 12, 14 may be formed of ceramics, composites, polymers, such as PEEK or UHMWPE, bone, including cortical, cancellous, allograft, autograft, xenograft, demineralized or partially demineralized bone, or any other materials appropriate to serve as load bearing supports. More preferably, the materials chosen for the endplates, in combination with the fluid, may be chosen so as to minimize wear.

Furthermore, preferably, any articulating surfaces in the intervertebral discs of the present invention includes a surface polish or similar wear reducing finish such as diamond finish, TiNi finish, etc. in order to minimize wear, decrease particle generation, and increase disc life.

The outer surface of the upper and lower endplates may be substantially flat, wedge-shaped, etc. The outer surfaces of the upper and lower endplates 12, 14 also may be dome shaped with their radii defined in the sagittal and coronal planes to generally match the shape of the ends of the adjacent vertebral, thereby providing a better fit in situ.

Figure 3A:
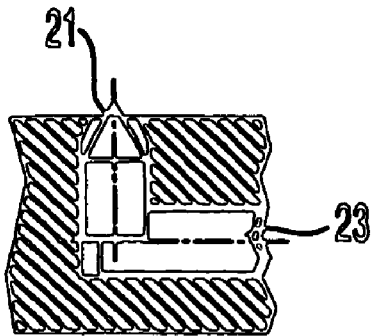
FIG. 3a is a side view of a deployable spike according to the present invention.
Figure 3B:
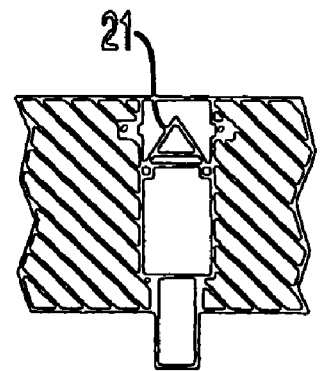
FIG. 3b is a side view of another deployable spike according to the present invention.
Figure 3C:
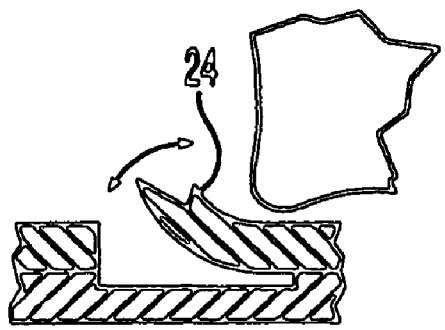
FIG. 3c is side view of a flexible spike according to the present invention.
Figure 3D:
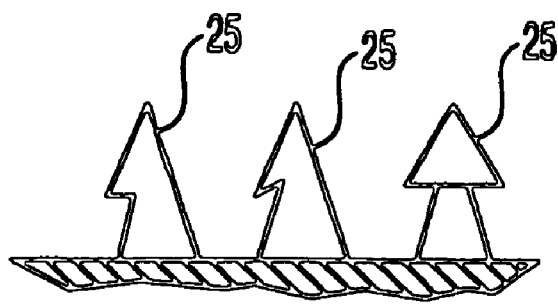
FIG. 3d is a side view of alternatively shaped teeth according to the present invention.
Figure 3E:
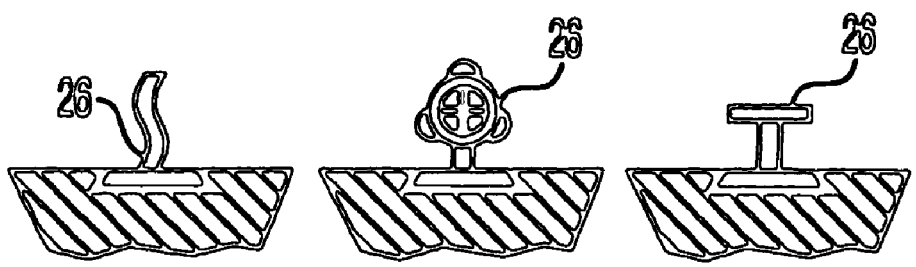
FIG. 3e is a side view of anchors according to the present invention.

In addition, as shown in FIGS. 1 through 2a, the disc 10 may include migration resistant features, such as, for example, spike-like structures 18 on the outer surfaces of the upper and lower endplates 12, 14. The migration resistant features may facilitate engagement of the disc 10 with the ends of the adjacent vertebra by providing a mechanical interlock as a result of penetration and/or deformation of the ends of the adjacent vertebrae. The initial mechanical stability afforded by spikes 18, for example, minimizes the risk of post-operative instability, movement, dislodging or expulsion of the disc 10. Other migration resistant features may include, without limitation, flaps, teeth, deployable teeth, deployable spikes, flexible spikes, flexible teeth, fins, insertable or expandable fins, anchors, screws, ridges, serrations, or other similar texturing on the outer surfaces of the upper and lower endplates 12, 14. As shown in FIG. 3a, deployable spikes 21 may be provided, and a cam mechanism 23 may be used to deploy the spikes 21. Alternatively, as shown in FIG. 3b, an instrument may be used to deploy the spikes 21. As shown in FIGS. 3c through 3e, respectively, examples of flexible spikes 24, shaped teeth 25, and anchors 26 are shown. Alternatively or in addition, bonding agents such as calcium phosphate cements, etc. may also be used to secure the disc 10 to adjacent vertebra.

Furthermore, the upper and lower endplates 12, 14 may also be coated with a bone growth inducing substance, such as hydroxypeptide, to promote bony ingrowth to permanently secure the disc 10 to the adjacent vertebrae. Alternatively, the upper and lower endplates 12, 14 may have a roughened or porous surface to facilitate bony ingrowth. Alternatively, the upper and lower endplates 12, 14 may have laser treated endplate layers to create a porous structure, or may integrate an osteoconductive/osteoinductive scaffold. The endplates 12, 14 may also be made from an osteoconductive and/or osteoinductive material to promote bony ingrowth. The endplates 12, 14 may further include a membrane and/or barrier to limit the depth of bony ingrowth permitted.

The upper and lower endplates 12, 14 may also have implant instrumentation attachment, guiding, and retaining structures. For example, the endplates 12, 14 may have holes, slots, threads, or a dovetail for accepting a tool used to implant the disc 10 and/or to distract the vertebrae. For example, the disc may include a slot formed in the upper and/or lower endplates 12, 14, the slot configured to receive an implant insertion instrument, a distractor or both.

As a result of the material and structural components used, the disc 10 can allow flexion/extension, lateral bending, axial rotation, and translation, depending on the loading imparted on the intervertebral disc. In addition, under the various spinal loading conditions resulting from spinal movements, the fluid 22 may move within the interior volume, either compressing (in the case of a gas), or moving radially outward as the membrane expands, allowing the end plates to move with respect to each other. This varying movement or displacement of fluid 22 provides a moving instantaneous axis of rotation.

Figure 4:
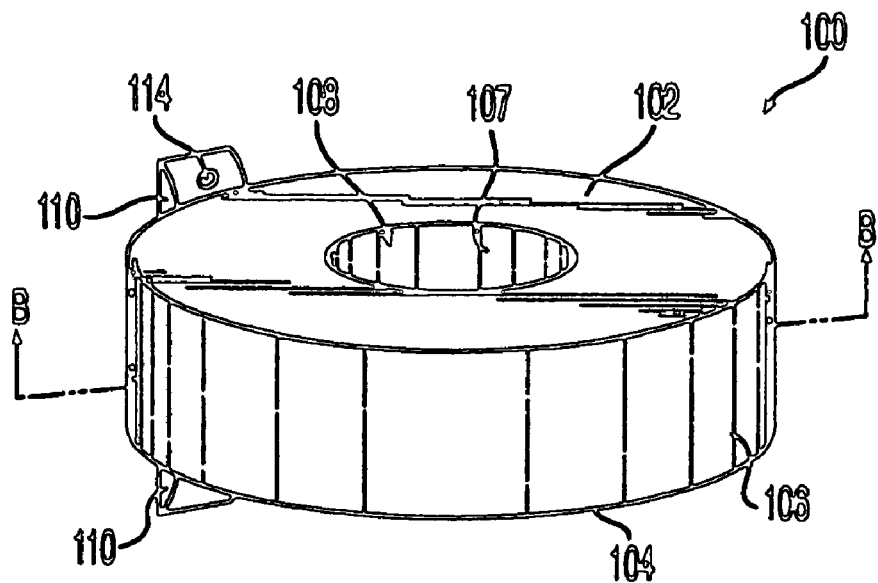
FIG. 4 is a perspective view of a second embodiment of an intervertebral disc according to the present invention.
Figure 5:
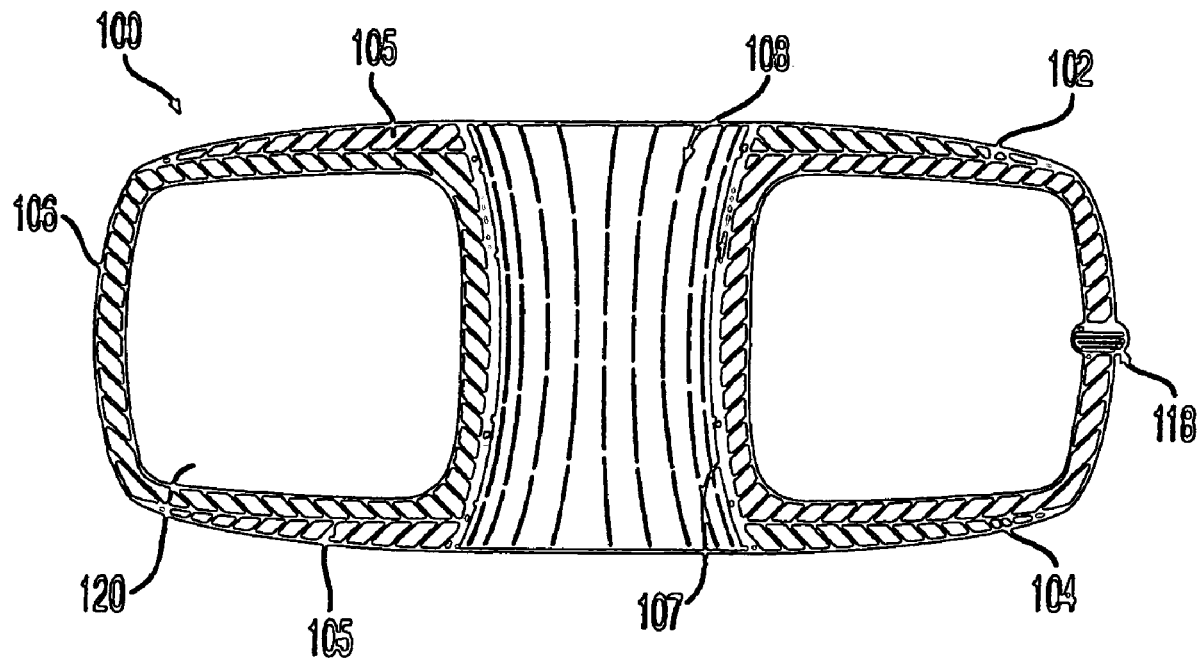
FIG. 5 is a cross-sectional view of the intervertebral disc of FIG. 4 taken along line B-B.

As shown in FIGS. 4 and 5, a second exemplary embodiment of an artificial disc is provided. Disc 100 generally has an annular shape and includes an upper surface 102, a lower surface 104, an outer sidewall 105 forming an outer wall, and an inner sidewall 107 defining an opening 103 (i.e., a thru-hole). However, the disc 100 may take on other shapes that preferably conform geometrically and anatomically with adjacent vertebral bodies, including, but not limited to, kidney-bean shape, circular, oval, ellipsoid, C-shape, D-shape etc. The disc 100 is preferably made from an elastomeric material that forms a closed reservoir having an interior volume 103. The disc 100 may further include a valve 118 for introducing or withdrawing fluid 120 from the interior volume 103 of disc 100 as previously described. Preferably, the valve 118 comprises a one-way valve and is located on the outer sidewall 105, as shown in FIG. 5, however, the valve 118 may also be located on the upper surface 102, the lower surface 104, or on the inner wall 107.

As best shown in FIG. 5, the disc 100 may further include a metal mesh 105 molded onto or otherwise secured to the upper surface 102 and/or lower surface 104. The metal mesh 103 may impart additional strength and rigidity to the disc 100. The metal mesh 105 may also be flexible so as to adopt to the concavity of the ends of the adjacent vertebral bodies to thereby facilitate a high degree of surface contact with the disc. The metal mesh 105 may also be textured, its surface may be porous, and it may be used in conjunction with bone growth inducing or conducting substances to further enhance engagement and fusion with the adjacent vertebral elements.

Preferably, the through-hole 108 may be filled with an elastomeric material (not shown). The elastomeric material may have a stiffness different from that of the disc 100. Preferably, the elastomeric material has a higher stiffness than the stiffness of disc 100 thereby allowing the through hole 108 to be more rigid and thus to act as a center pivot or center strut about which the upper and lower surfaces 102, 104 may articulate. The center pivot may allow one portion or side of the disc 100 to compress while at the same time permitting another portion of the disc 100 to expand. In an alternative embodiment, the elastomeric material may have a lower stiffness than the stiffness of disc 100. Alternatively, the through-hole 108 may be filled with a hydrogel.

In addition, the upper and lower surfaces 102, 104 of disc 100 may include migration resistant features, permanent fixation means and/or implant instrumentation attachment, guiding, and retaining structures as previously described in regards to the disc 10 of FIGS. 1 through 3. Preferably, disc 100 may be provided with at least one securing features (i.e., flap) 110 to facilitate engagement of the disc 100 with the vertebral bodies of the adjacent vertebra. As shown in FIG. 4, preferably two flaps 110 are provided, one flap 110 for the upper surface 102 and one flap 110 for the lower surface 104. Flaps 110 may be provided as one piece which extends beyond the upper and lower surfaces 102, 104, or flaps 110 may be provided as two or more pieces. Flaps 110 preferably extend above and below surfaces 102, 104, respectively, from lateral side 106, and are sized to abut a portion of the exterior surface of the vertebral bodies of the adjacent vertebrae. Flaps 110 may include through-holes 114 for receiving fasteners such as, for example, fixation screws (not shown). The fixation screws can be used to secure disc 100 to the vertebral bodies of the adjacent vertebrae.

Figure 6:
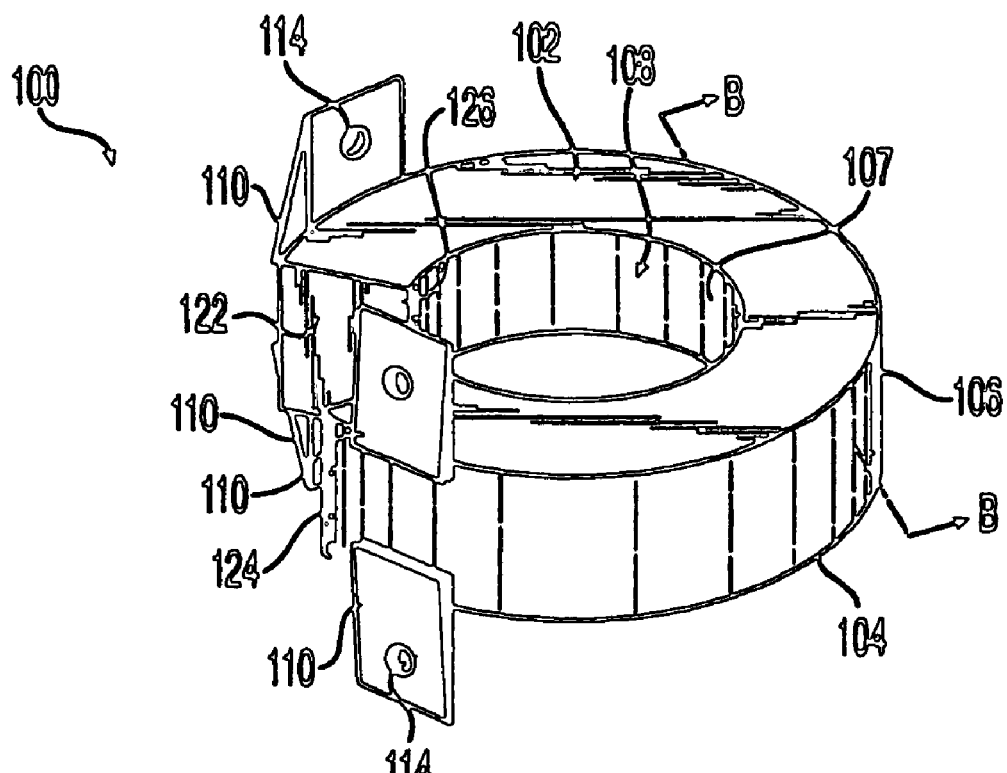
FIG. 6 is a perspective view of an alternative embodiment of the intervertebral disc of FIG. 4.

Alternatively, as shown in FIG. 6, disc 100 may further include a gap 126 in its circumference, producing opposed end faces 122, 124 which give the disc 100 a general "C" shaped appearance. Preferably, end faces 122, 124 are configured to be resiliently biased apart, however, end faces 122, 124 may be naturally disposed apart from each other, without resilient biasing. The gap 126 formed between end faces 122, 124 provide the disc 100 with increased flexibility thus facilitating insertion and placement of the disc 100 between vertebrae. The gap 126 permits the diameter of disc 100 to be decreased by pressing ends 122, 124 together. The gap 126 also may allow the disc to be unfolded by pulling ends 122, 124 apart. Thus, the gap 126, allows the disc 100 to be configured to have at least one smaller outer dimension as compared to its rest state, which in turn may allow the disc 100 to be inserted into an anatomical region through a cavity or other opening that is smaller than the uncompressed (i.e. at rest) size of disc 100, thus making posterior insertion possible.

Depending on the location of the spine where the disc 100 is implanted, the disc 100 preferably restores height, lordosis, stiffness, offers compression stiffness, and allows a range of motion similar to that described in relation to previous embodiments.

As a result of the materials, geometry, and components used, disc 100 can allow flexion/extension, lateral bending, axial rotation, and translation, depending on the loading imparted on the intervertebral disc. Similar to the embodiment of FIGS. 1 through 2a, under various spinal loading conditions resulting from spinal movements, the fluid 22 may move within the interior volume, either compressing (in the case of a gas), or moving radially outward as the membrane expands, allowing the end plates to move with respect to each other. This varying movement or displacement of fluid 22 provides a moving instantaneous axis of rotation.

Figure 7:
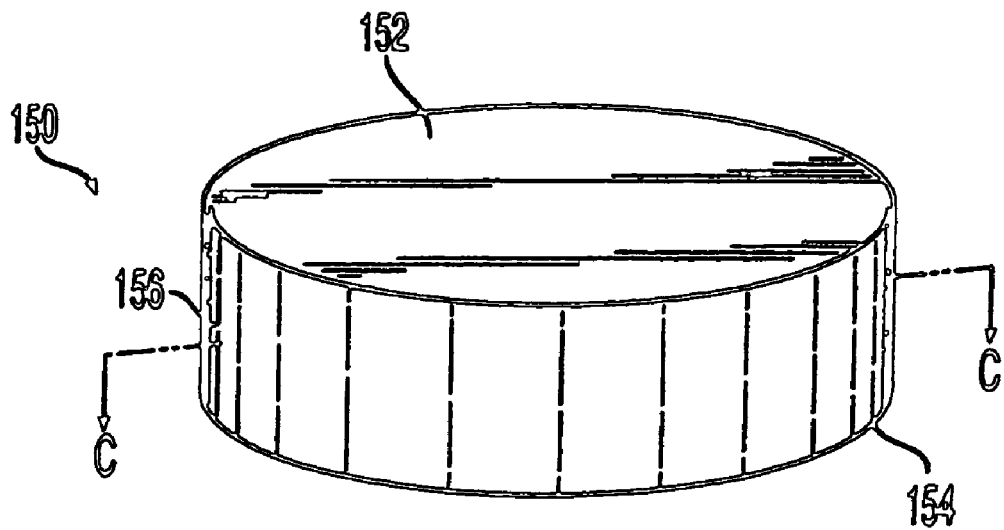
FIG. 7 is a perspective view of a third embodiment of an intervertebral disc according to the present invention.
Figure 8:
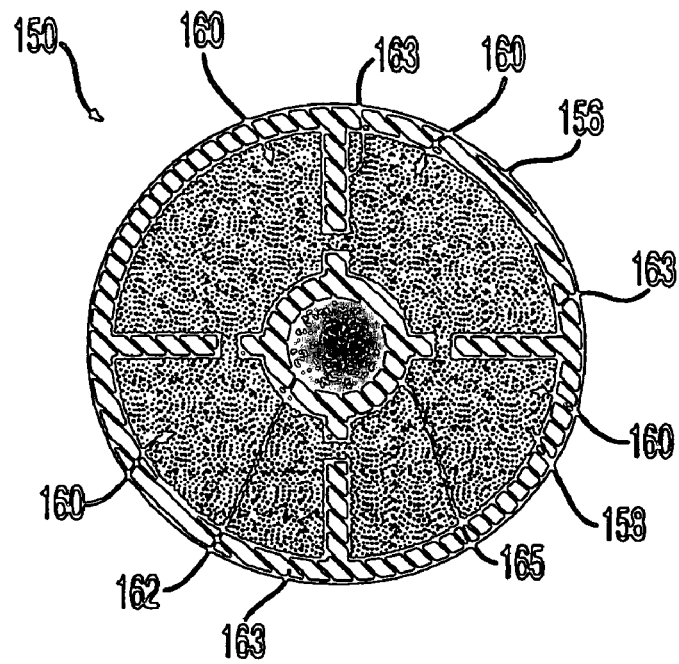
FIG. 8 is a cross-sectional view of the intervertebral disc of FIG. 7 taken along line C-C.
Figure 9:
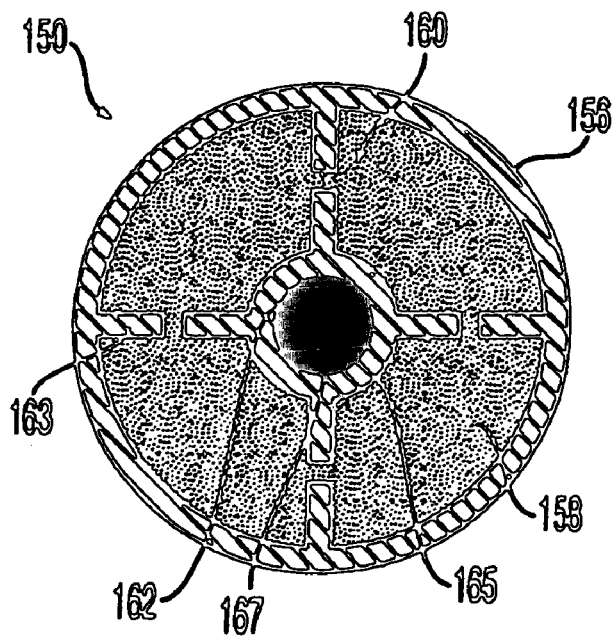
FIG. 9 is a cross-sectional view of an alternative embodiment of the intervertebral disc of FIG. 7 taken along line D-D.

With reference to FIGS. 7 through 9, a third exemplary embodiment of an artificial disc will be described. Preferably, disc 150 has a generally cylindrical shape with a circular footprint and has an upper end 152, a lower end 154, and an outer sidewall 156 disposed therebetween. The disc further includes an interior volume as defined between the upper and lower ends 152, 154 and the outer sidewall 156. Although illustrated as a cylinder, the disc 150 may take on any other shape that preferably conform geometrically and anatomically with adjacent vertebral bodies, including, but not limited to, kidney-bean shaped, annular, oval, ellipsoid, D-shaped, C-shaped, etc.

The disc 150 may be made from any material known in the art capable of serving as a load bearing support including, but not limited to, elastomers, polymers, ceramics, composites, etc. The disc 150 may further include a valve (not shown) for introducing fluid 158 into the interior of disc as previously described in relation to other embodiments.

The disc 150 may further include upper and lower end plates (not shown) as previously described with regards to other embodiments. Alternatively, the disc 150 may include a metal mesh molded onto or otherwise secured to the upper surface 152 and/or lower surface 154 as previously described in relation to other embodiments. In addition, the disc 150 may further include migration resistant features, permanent fixation means and/or implant instrumentation attachment, guiding, and retaining structures as previously described in relation to other embodiments.

Depending on the location of the spine where the disc 150 is implanted, the disc 150 preferably restores height, lordosis, stiffness, offers compression stiffness, and allows a range of motion similar to that described in relation to previous embodiments.

With reference to FIG. 8, the interior of disc 150 is shown. Preferably the interior of disc 150 includes a plurality of interconnected peripheral chambers 160 and a separate central chamber 162. The multi-chambered interior of disc 150 permits controlled fluid flow within the intervertebral disc 150 so that under loading, controlled articulation or motion is permitted. The peripheral chambers 160 may be in fluid communication with the central chamber 162 by way of an open passageway, a porous central wall 165, an osmotic membrane, etc. Preferably, however, the peripheral chambers 160 are in fluid communication with the central chamber 162 by way of a baffle and/or valve. More preferably, the baffle and/or valve is configured to provide for selective exchange of fluid such that the fluid 158 from the peripheral chambers 160 may flow more easily or quickly into the central chamber 162 than the fluid 158 would flow out of the central chamber 162. Alternatively, the central chamber 162 may be sealed with respect to the peripheral chambers 160. In this case, the peripheral chamber 160 and central chamber 162 may be filled with the same or different fluids.

The peripheral chambers 160 are defined by walls 163, while the central chamber 162 is separated from the peripheral chambers 160 by a central wall 165. In addition to defining the geometry of chambers 160, 162, walls 163, 165 also serve as supports between surfaces 152, 154 by resisting loads acting upon the disc 150 when in use.

Preferably the central chamber 162 and outer periphery chambers 160 are arranged so that the central chamber 162 is more rigid than the center peripheral chambers 160 (such as by completely filling with incompressible fluid), thus enabling the central chamber 162 to act as a center pivot or center strut about which the upper and lower surfaces 152, 154 may articulate. The center pivot allows one portion or side of the disc 150 to compress while at the same time permitting another portion of the disc 150 to expand. The walls 163 of the peripheral chambers 160 may be formed of a material having a lower stiffness than the material used to produce the central wall 165, thereby allowing the central chamber 162 to be more rigid and act as a center pivot. Alternatively, the walls 163 of the peripheral chambers 160 may be formed of the same material as the central wall 165, but with a geometry that provides a lower stiffness than the geometry of the central wall 165 of central chamber 162 thereby allowing the central chamber 162 to act as a center pivot for disc 150. Furthermore, a combination of material and geometric characteristics of the chamber walls 163, 165 may be selected to make the central chamber 162 more rigid than the peripheral chambers 160 so that the central chamber 162 may act as a center pivot about which the disc 150 pivot.

The geometry of chambers 160, 162, the geometry and material of the walls 163, 165, along with the fluid(s) disposed therein can be selected to obtain the desired characteristics of the disc, including the desired stiffness, height, pliability, and preferably the relative stiffness of the central chamber 162 with respect to the peripheral chambers 160 to provide the desired articulation between the upper and lower ends 152, 154. Thus, the disc 150 will move, deform or extend in flexion/extension, lateral bending, axial rotation, and translation depending on the loadings imparted on the intervertebral disc since under various spinal loading conditions, the fluid can translate between the peripheral chambers 160 and/or the central chamber 162. This movement of the chambers with respect to each other, as well as the movement of the fluid within and between the chambers allows for a moving instantaneous axis of rotation of the disc 150. It should be noted that the central chamber 162 needn't be located in the center of the disc, but rather may be positioned in any other location within the disc appropriate to produce the desired movement of the endplates relative to each other.

Alternatively, as shown in FIG. 9, the central chamber 162 may have a spring 167. The spring 167 serves as additional support for disc 150 further enabling the central chamber 162 to act as a center pivot and/or strut. When a spring 167 is provided in the central chamber 162, fluid may or may not also be provided. The spring 167 may be formed from any material known in the art, for example, cobalt-chromium alloys, titanium alloys, stainless steel, amorphous alloys, polymers, or composites.

Alternatively, the central chamber 162 may house a bladder (not shown). The bladder may be integrally formed with, or connected to, ends 152, 154. Alternatively, the bladder may be separate from the ends 152, 154. This bladder may articulate, compress, and/or translate within the central chamber 162, providing the disc with a moving instantaneous axis of rotation, which under various loading conditions, may allow for a greater degree of articulation or movement of disc 150. In addition, the central bladder may serve as additional support for disc 150 so that the central chamber 162 may act a center pivot and also permit the desired motion.

Figure 10:
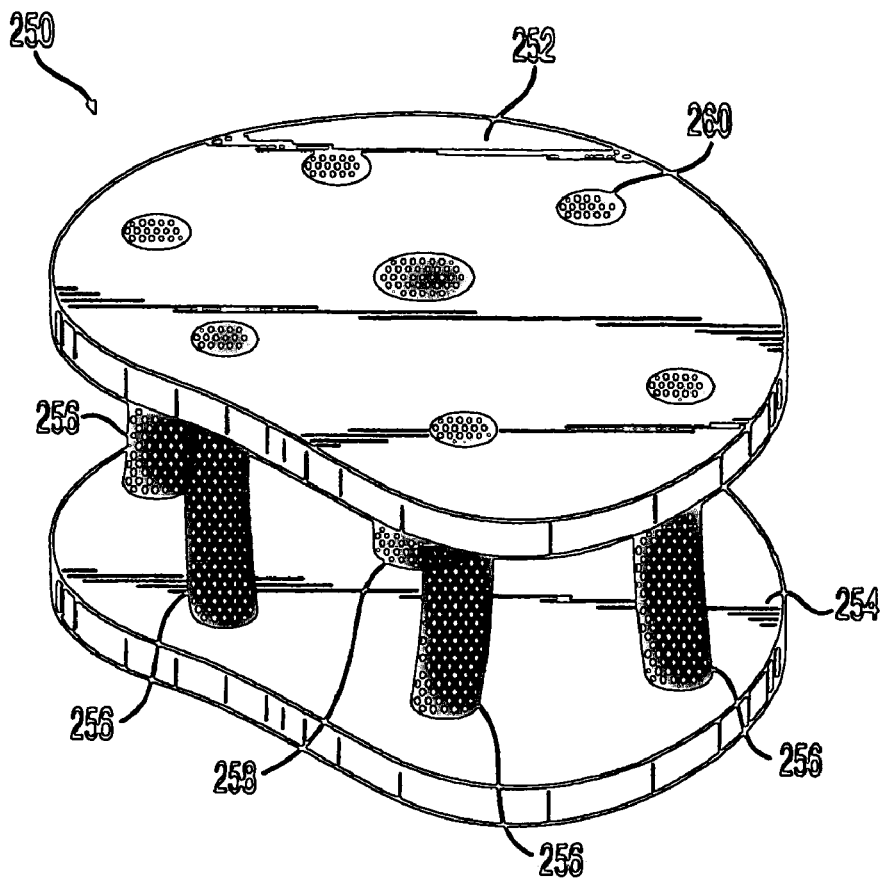
FIG. 10 is a perspective view of a fourth embodiment of an intervertebral disc according to the present invention.
Figure 11:
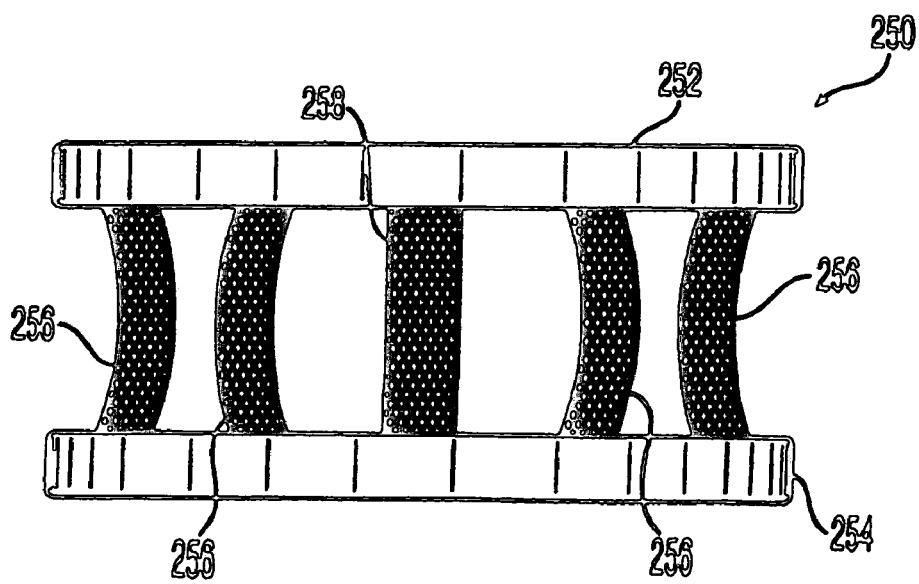
FIG. 11 is a side view of the fourth embodiment of the intervertebral disc of FIG. 12.

With reference to FIGS. 10 and 11, a fourth embodiment of an artificial intervertebral disc will be described. Disc 250, has a generally kidney-bean shaped footprint with an upper endplate 252, a lower endplate 254, and at least one cable element 256, 258. Although disc 250 is shown as having a kidney-bean shaped footprint, the disc 250 may take on any other shape that generally conforms geometrically and anatomically with adjacent vertebral bodies, including, but not limited to, circular, annular, oval, ellipsoidal, D-shaped, C-shaped, etc. In addition, the endplates 252, 254 preferably include migration resistant features, permanent fixation means and/or implant instrumentation attachment, guiding, and retaining structures as previously described in relation to previous embodiments.

Preferably, the upper and lower endplates 252, 254 are formed of metal, such as titanium, stainless steel, titanium alloys, cobalt-chromium alloys, or amorphous alloys. Alternatively, the upper and lower endplates 252, 254 may be formed of ceramics, composites, polymers, such as PEEK or UHMWPE, bone, including cortical, cancellous, allograft, autograft, xenograft, demineralized or partially demineralized bone, or any other materials appropriate to serve as load bearing supports.

The outer surface of the upper and lower endplates may be substantially flat, wedge-shaped, etc. Alternatively, the outer surfaces of the upper and lower endplates 252, 254 may be dome shaped with their radii defined in the sagittal and coronal planes to generally match the shape of the ends of the adjacent vertebral, thereby providing a better fit in situ.

The disc 250 may also include an elastic membrane, the elastic membrane generally extending from the upper endplate 252 to the lower endplate 254 as previously described in relations to previous embodiments. The disc 250 may also include a valve, the valve providing access to the interior of the disc 250 so that a fluid may be at least partially injected into the interior of the disc as described in relation to previous embodiments.

Depending on the location of the spine where the disc 250 is implanted, the disc 250 preferably restores height, lordosis, stiffness, offers compression stiffness, and allows a range of motion similar to that described in relation to previous embodiments.

As shown, disc 250 includes a plurality of peripheral cable elements 256 and a central cable element 258. The peripheral cable elements 256 may be located near the perimeter of disc 250, while the center cable element 258 is preferably located near the center of the disc. The peripheral cable elements 256 and the center cable element 258 are attached to the upper and lower endplates 252, 254 by any fixation means know in the art including, but not limited to, bonding agents, ultrasonic welding, screws, nails, mechanical wedging and pins. Preferably, however, the cable elements 256, 258 engage the upper and lower endplates 252, 254 via boreholes 260 formed on the upper and lower endplates 252, 254. The ends of cable elements 256, 258 are crimped where they penetrate the outer surface of the upper and lower endplates 252, 254. This permits surgeons to appropriately size the disc 250 just prior to implantation by means of crimping/attaching appropriately sized cables to the endplates. The peripheral cable elements 256 and central cable element 258 may be made from metals, polymers, composites, or any other appropriate material known in the art.

In one embodiment, the center cable element 258 is shorter than the peripheral cable elements 256. This causes the peripheral elements 256 to assume a curved or bowed shape between the endplates 252, 254. As a result, the length of the central cable element 258 determines the maximum distance between the upper and lower endplates 252, 254 under tension. Furthermore, as a result of the peripheral cable elements 256 being longer than the central cable element 258, the shorter central cable element 258 causes the longer peripheral cable elements 256 to be held in compression. The resilience of the bowed peripheral cable elements 256 provides shock absorption, axial compression and articulation characteristics to the disc 450.

As a result of the materials, geometry, and components used, disc 250 can allow flexion/extension, lateral bending, axial rotation, and translation, depending on the loading conditions. In addition, under various spinal loading conditions resulting from spinal movements, the peripheral cable elements 256 can bend or compress varying amounts. Such variable bending/compression provides the desired moving instantaneous axis of rotation.

Figure 12:
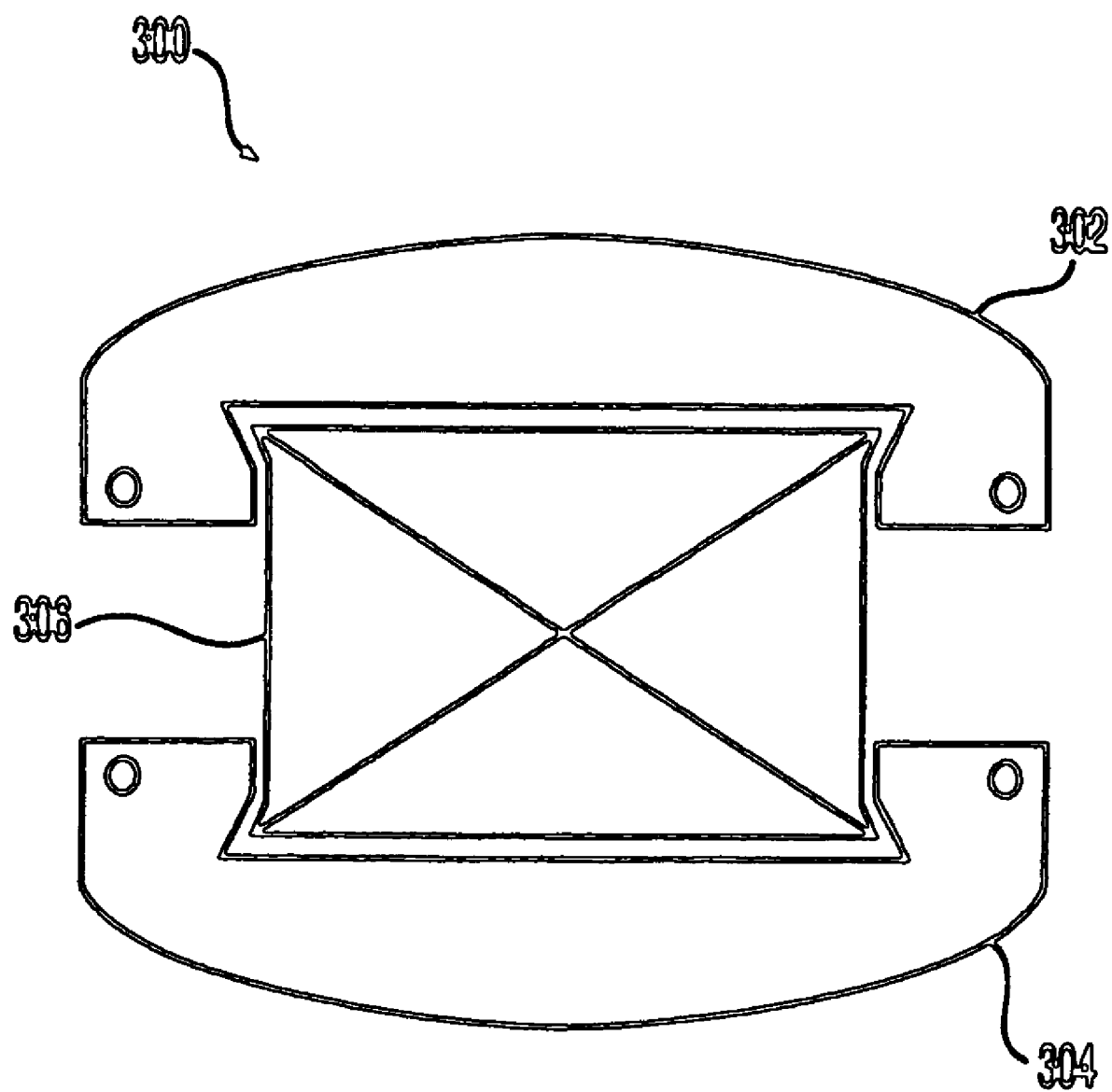
FIG. 12 is schematic view of a fifth embodiment of an intervertebral disc according to the present invention.

With reference to FIG. 12, an exemplary installation procedure will be described. Generally speaking the disc 300 includes an upper endplate 302, a lower endplate 304 and a core mechanism 306, the core mechanism being any cable, elastomer, fiber, or fluid filled disc previously described. The intervertebral discs 300 may be implanted in a modular fashion, for example, the endplates 302, 304 of disc 300 are inserted into the intervertebral cavity using instruments such as a distractor and/or holder instrument. The intervertebral disc space may be distracted using a standard spinal distractor which engages the endplates 302, 304. Trial spacers are then preferably used to determine the appropriate size of the core mechanism 306 to be inserted in the resulting disc space. In an exemplary embodiment, the core mechanism, 306 is inserted and attached to endplates 302, 304 through the use of a dovetail, slot, or similar connection. This modular insertion technique avoids over-distracting the intervertebral space, which may damage surrounding tissue and/or blood vessels.

Alternatively, the intervertebral disc 300 may be inserted preassembled with the use of particular insertion tools. For example, an endplate holding clip may be used that allows the endplates 302, 304 to be held and locked in a parallel and spaced relationship as they are inserted into the intervertebral space. Once implanted, the clip may be unlocked and removed from the endplates 302, 304. The clip may then be removed from the intervertebral space. In addition, the disc 300 may be implanted in a compressed state to prevent over-distraction. The introduction of the disc 300 in a compressed state may be accomplished via a surgical insertion instrument or by an internal mechanism located in the disc 300.

An anterior, lateral, or anterolateral surgical approach may be used for the intervertebral disc 300. Furthermore, depending on the intervertebral disc 300 to be implanted, a minimally invasive surgical method or a simultaneous distraction and implantation surgical method may be used. Simultaneous distraction and implantation may be accomplished, for example, by using slots formed on the outer surface of the endplates 302, 304 to guide the implant down the distractor during implantation. Also, depending on the intervertebral disc to be implanted, an artificial Anterior Longitudinal Ligament or the natural Anterior Longitudinal Ligament may be attached directly to the disc or to the adjacent vertebral bodies. Attachment of the Anterior Longitudinal Ligament may assist in preventing movement, dislodging or expulsion of the implant. To assist with the implantation of the intervertebral disc, the intervertebral discs may include alignment markers.

While various descriptions of the present invention are described above, it should be understood that the various features can be used singly or in combination thereof. Therefore, this invention is not to be limited to the specific preferred embodiments depicted herein.

Further, it should be understood that variations and modifications within the spirit and scope of the invention may occur to those skilled in the art to which the invention pertains. For example, some portions of the implants disclosed herein may be formed of bone, such as allografts, autografts, and xenografts, which may be partially or fully demineralized. In addition, some implants may include bone material or other bone growth inducing material in their interiors or on/in their endplates. Such substances in the interiors may be permitted to interact with the surrounding anatomy, as with channels or other holes formed in the implant walls. Also, intra and post-operative alignment markers may be used to assist with implantation of the intervertebral discs. Furthermore, the intervertebral discs can be made rigid in situations where fusion is necessary. The intervertebral discs may be made rigid by, for example, allowing fusion between the endplates, inserting spacers between the endplates, or by injecting a solidifying liquid between the endplates. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An intervertebral disc for placement between first and second vertebrae, the intervertebral disc comprising:
   an upper surface for contacting the first vertebra;
   a lower surface for contacting the second vertebra;
   an exterior wall having an inner surface and an outer surface, the exterior wall extending between the upper and lower surfaces; and
   an interior volume defined between the upper and lower surfaces and the inner surface of the exterior wall, the interior volume including a central chamber surrounded by a plurality of interconnected peripheral chambers, the plurality of interconnected peripheral chambers being sealed from the central chamber,
   wherein the central chamber has a stiffness, and the plurality of peripheral chambers has a stiffness less than the stiffness of the central chamber.

2. The intervertebral disc of claim 1, wherein the central chamber has a first fluid disposed therein and the plurality of interconnected peripheral chambers have a second fluid disposed therein.

3. The intervertebral disc of claim 2, further comprising:
   a valve in communication with the plurality of interconnected peripheral chambers for at least partially filling the plurality of interconnected peripheral chambers with the second fluid.

4. The intervertebral disc of claim 3, wherein at least a portion of the valve is disposed within the exterior wall.

5. The intervertebral disc of claim 1, wherein the central chamber is defined by a first wall, and the plurality of peripheral chambers are disposed between the exterior wall and the first wall.

6. The intervertebral disc of claim 5, wherein the first wall is formed of a first material having a first stiffness and the exterior wall is formed of a second material having a second stiffness.

7. The intervertebral disc of claim 5, wherein the first wall has a first configuration with a first stiffness and the exterior wall has a second configuration with a second stiffness.

8. The intervertebral disc of claim 1, wherein the central chamber has a resilient element disposed therein.

9. The intervertebral disc of claim 8, wherein the disc has a stiffness and the resilient element is a spring.

10. The intervertebral disc of claim 1, wherein the central chamber has a bladder disposed therein.

11. The intervertebral disc of claim 1, wherein the disc is constructed of a material selected from the group consisting of an elastomer, a polymer, a ceramic, a composite and a metal mesh.

12. The intervertebral disc of claim 1, further comprising: a metal mesh secured to the upper and lower surfaces.

13. The intervertebral disc of claim 1, further comprising: an upper endplate secured to the upper surface and a lower endplate secured to the lower surface.

14. The intervertebral disc of claim 13, further comprising: migration-resistant structures disposed on the upper and lower endplates.

15. The intervertebral disc of claim 13, further comprising: permanent fixation means disposed on the upper and lower endplates.

16. The intervertebral disc of claim 1, further comprising: migration-resistant structures disposed on at least one of the surfaces.

* * * * *